(12) United States Patent
Helson

(10) Patent No.: US 7,912,689 B1
(45) Date of Patent: Mar. 22, 2011

(54) ENHANCING STRUCTURE DIAGRAM GENERATION THROUGH USE OF SYMMETRY

(75) Inventor: Harold E. Helson, Arlington, MA (US)

(73) Assignee: Cambridgesoft Corporation, Cambridge, MA (US)

( * ) Notice: Subject to any disclaimer, the term of this patent is extended or adjusted under 35 U.S.C. 154(b) by 0 days.

(21) Appl. No.: 09/502,133

(22) Filed: Feb. 11, 2000

Related U.S. Application Data

(60) Provisional application No. 60/119,654, filed on Feb. 11, 1999.

(51) Int. Cl.
*G06F 7/48* (2006.01)
*G06G 7/60* (2006.01)

(52) U.S. Cl. ............................................. 703/12; 703/2

(58) Field of Classification Search ................... 703/12, 703/11, 9, 5, 6, 2, 1
See application file for complete search history.

(56) References Cited

U.S. PATENT DOCUMENTS

| | | | |
|---|---|---|---|
| 4,473,890 A | 9/1984 | Araki et al. | |
| 4,747,059 A | 5/1988 | Hirayama et al. | |
| 4,811,217 A * | 3/1989 | Tokizane et al. | 707/3 |
| 4,908,781 A * | 3/1990 | Levinthal et al. | 702/30 |
| 5,025,388 A * | 6/1991 | Cramer et al. | 700/293 |
| 5,157,736 A * | 10/1992 | Boyer et al. | 702/31 |
| 5,249,137 A * | 9/1993 | Wilson et al. | 703/2 |
| 5,345,516 A * | 9/1994 | Boyer et al. | 702/31 |
| 5,379,234 A * | 1/1995 | Wilson et al. | 703/11 |
| 5,418,944 A | 5/1995 | DiPace et al. | |
| 5,424,963 A * | 6/1995 | Turner et al. | 703/6 |
| 5,434,796 A * | 7/1995 | Weininger | 703/12 |
| 5,448,498 A * | 9/1995 | Namiki et al. | 702/138 |
| 5,461,580 A * | 10/1995 | Facci et al. | 703/2 |
| 5,486,995 A | 1/1996 | Krist et al. | |
| 5,577,239 A | 11/1996 | Moore et al. | |
| 5,619,421 A * | 4/1997 | Venkataraman et al. | 702/27 |
| 5,699,268 A * | 12/1997 | Schmidt | 702/27 |
| 5,740,072 A * | 4/1998 | Still et al. | 703/11 |

(Continued)

FOREIGN PATENT DOCUMENTS

JP 401161578 6/1989

(Continued)

OTHER PUBLICATIONS

Barsamian, S.T.; Barsamian, T.K, "Dielectric phenomenon of living matter," IEEE Transactions on Dielectrics and Electrical Insulation, vol. 4 Issue: 5, Oct. 1997, pp. 629-643.*

(Continued)

*Primary Examiner* — Hugh Jones
(74) *Attorney, Agent, or Firm* — Wilmer Cutler Pickering Hale & Dorr LLP.

(57) ABSTRACT

A method and a system are provided for enhancing structure diagram generation ("SDG"). In SDG, aesthetic two-dimensional ("2-D") coordinates for use in a diagrammatic representation ("diagram") of a molecule are derived from a connection table for the molecule. SDG may also improve the aesthetic qualities of a chemical structure diagram having existing coordinates, if available. SDG is enhanced by expressing the symmetry present in the molecule, by making use of symmetry in the 2-D dynamics used to lay out rings and chains, by construction of bridges using an open polygon method together with a potential function, and by an elegant approach to the relative positioning of molecules ("free rectangle method").

25 Claims, 13 Drawing Sheets

Microfiche Appendix Included
(1 Microfiche, 33 Pages)

U.S. PATENT DOCUMENTS

| | | | |
|---|---|---|---|
| 5,740,425 A | 4/1998 | Povilus | |
| 5,778,377 A | 7/1998 | Marlin et al. | |
| 5,841,678 A | 11/1998 | Hasenberg et al. | |
| 5,851,272 A | 12/1998 | Vicenzi | |
| 5,854,992 A * | 12/1998 | Shakhnovich et al. | 702/27 |
| 5,874,564 A | 2/1999 | Ecker et al. | |
| 5,940,807 A | 8/1999 | Purcell | |
| 5,950,192 A | 9/1999 | Moore et al. | |
| 5,956,711 A | 9/1999 | Sullivan et al. | |
| 5,978,804 A | 11/1999 | Dietzman | |
| 5,978,848 A | 11/1999 | Maddalozzo, Jr. et al. | |
| 5,980,096 A * | 11/1999 | Thalhammer-Reyero | 703/13 |
| 6,007,691 A | 12/1999 | Klock, Jr. | |
| 6,014,449 A * | 1/2000 | Jacobs et al. | 702/27 |
| 6,023,659 A | 2/2000 | Seilhamer et al. | |
| 6,023,683 A | 2/2000 | Johnson et al. | |
| 6,038,562 A | 3/2000 | Anjur et al. | |
| 6,055,516 A | 4/2000 | Johnson et al. | |
| 6,061,636 A | 5/2000 | Horlbeck | |
| 6,081,789 A | 6/2000 | Purcell | |
| 6,119,104 A | 9/2000 | Brumbelow et al. | |
| 6,125,383 A * | 9/2000 | Glynias et al. | 709/202 |
| 6,128,582 A * | 10/2000 | Wilson et al. | 702/27 |
| 6,128,619 A | 10/2000 | Fogarasi et al. | |
| 6,178,384 B1 * | 1/2001 | Kolossv.ang.ry | 702/27 |
| 6,185,506 B1 * | 2/2001 | Cramer et al. | 702/22 |
| 6,185,548 B1 * | 2/2001 | Schwartz et al. | 702/27 |
| 6,189,013 B1 | 2/2001 | Maslyn et al. | |
| 6,199,017 B1 | 3/2001 | Tomonaga et al. | |
| 6,219,622 B1 * | 4/2001 | Schmidt | 702/27 |
| 6,226,620 B1 | 5/2001 | Oon et al. | |
| 6,236,989 B1 | 5/2001 | Mandyam et al. | |
| 6,240,374 B1 | 5/2001 | Cramer et al. | |
| 6,246,410 B1 | 6/2001 | Bergeron et al. | |
| 6,256,647 B1 | 7/2001 | Toh et al. | |
| 6,272,472 B1 | 8/2001 | Danneels et al. | |
| 6,295,514 B1 | 9/2001 | Agrafiotis et al. | |
| 6,311,134 B1 | 10/2001 | Sorenson | |
| 6,319,668 B1 | 11/2001 | Nova et al. | |
| 6,323,852 B1 | 11/2001 | Blower, Jr. et al. | |
| 6,324,522 B2 | 11/2001 | Peterson et al. | |
| 6,326,962 B1 | 12/2001 | Szabo | |
| 6,332,138 B1 * | 12/2001 | Hull et al. | 707/3 |
| 6,341,314 B1 | 1/2002 | Doganata et al. | |
| 6,453,064 B1 | 9/2002 | Aikawa et al. | |
| 6,505,172 B1 | 1/2003 | Johnson et al. | |
| 6,519,611 B1 * | 2/2003 | Zong | 707/104.1 |
| 6,542,903 B2 * | 4/2003 | Hull et al. | 707/104.1 |
| 6,571,245 B2 | 5/2003 | Huang et al. | |
| 6,582,233 B1 * | 6/2003 | Clark | 434/278 |
| 6,584,412 B1 | 6/2003 | Brecher | |
| 6,618,852 B1 | 9/2003 | van Eikeren et al. | |
| 6,631,381 B1 | 10/2003 | Couch et al. | |
| 6,654,736 B1 * | 11/2003 | Ellis et al. | 707/104.1 |
| 6,665,685 B1 | 12/2003 | Bialic | |
| 6,675,105 B2 | 1/2004 | Hogarth et al. | |
| 6,678,577 B1 | 1/2004 | Stylli et al. | |
| 6,721,754 B1 | 4/2004 | Hurst et al. | |
| 6,751,615 B2 | 6/2004 | Nisler et al. | |
| 6,871,198 B2 | 3/2005 | Neal et al. | |
| 6,884,394 B1 | 4/2005 | Hehenberger et al. | |
| 7,054,754 B1 | 5/2006 | Brecher | |
| 7,295,931 B1 | 11/2007 | Helson | |
| 7,356,419 B1 | 4/2008 | Culot et al. | |
| 2002/0049548 A1 | 4/2002 | Bunin | |
| 2002/0165853 A1 | 11/2002 | Gogolak | |

FOREIGN PATENT DOCUMENTS

| | | |
|---|---|---|
| WO | WO 99/58474 | 11/1999 |

OTHER PUBLICATIONS

Casey et al., "Optical recognition of chemical graphics," Proceedings of the Second International Conference on Document Analysis and Recognition, Oct. 20-22, 1993, pp. 627-631.*

Morrison et al., Organic Chemistry, Allyn and Bacon, Inc. Boston, 1973, show how to determine chemical structure diagrams. p. 261-262.*

ChemDraw and Chem3D version History, 8 pages of version history dating back to 1985.*

CambridgeSoft Solutions Products Overview, 28 pages describing their product lines.*

Hu et al.; Computer perception of topological symmetry by all-paths algorithm; abstract; Jan. 18, 1999; Chemometrics and Intelligent Laboratory Systems.*

Shelley et al.; An approach to the assignment of canonical connection tables and topological symmetry perception; p. 247; 1979; J. Chem. Inf. Comput. Sci.*

Fan et al.; Detection of constitutionally equivalent sites from a connection table; pp. 654-659; J. Chem. Inf. Comput. Sci.; 1996.*

Zlatina et al: Generation and Representation of Stereoisomers of a Molecular Structure; All-Union Scientific-Research Institute of Organic Synthesis. Translated from Zhurnal Strukturnoi Khimii, vol. 32, No. 4, pp. 92-97, Jul.-Aug. 1991. Original article submitted Jan. 18, 1990 on Face of document pp. 538-533.*

Bohanec: Structure Generation of Constitutional Isomers from Structural Fragments: J. Chem. Inf. Comput. Sci. 1991, 31, 531-540.*

Jorgensen: CAMEO: a program for the logical prediction of the products of organic reactions; Pure & Appl. Chem., vol. 62, No. 10, pp. 1921-1932,1990. 1990 IUPAC.*

Razinger, M. et al., "Graph Automorphism Perception Algorithms in Computer-Enhanced Structure Elucidation," *J. Chem. Inf., Comput. Sci. 33*(197) (1993).

Helson, Ph.D., H.E., "Simulation of Carbene Chemistry and Other Problems in Computer-Assisted Organic Synthesis," Thesis, Purdue University (1993).

Helson, H.E., et al., "Computer-Assisted Mechanistic Evaluation of Organic Reactions. 25. Structure Diagram Positioning," *J. Chem. Inf., Comput. Sci. 34*(962) (1993).

Lipkowitz, Kenny B. and Donald B. Boyd, "Reviews in Computational Chemistry vol. 13," Wiley-VCH, Inc.. 1999.

"CSC Chemical Finder™ Chemical Information Management" *User's Guide.* Version 1.0 for Apple Macintosh. Cambridge Scientific Computing, Inc. 1991-1992.

"CS ChemFinder™ Searching and Information Integration" *User's Guide.* CS ChemFinder Pro and CS ChemFinder. Version 2.0 for Apple Macintosh. CambridgeSoft Corporation. 1991-1995.

"ChemDraw® Chemical Structure Drawing Standard." *User's Guide.* CS ChemDraw 4.5 for Windows and Macintosh. CambridgeSoft Corporation. 1986-1997.

"ChemFinder Searching and Information Integration" *User's Guide.* CS ChemFinder 4.0 for Windows and Macintosh (3.0). CambridgeSoft Corporation. 1986-1997.

"CS ChemDraw™ for Apple Macintosh" *Quick Reference.* CambridgeSoft Corporation. 1986-1996.

"Chem3D™ The Molecular Modeling System" Version 3.0. Cambridge Scientific Computing, Inc. 1986-1990.

"CSC Chem3D™ Molecular Modeling and Analysis." *Tutorial.* CSC Chem3D and CSC Chem3D Plus. Version 3.1 for Apple Macintosh. Cambridge Scientific Computing, Inc. 1986-1993.

"Chem3D® Molecular and Analysis" *User's Guide.* CS Chem3D 4.0 for Windows and Macintosh. Cambridge Soft Corporation. 1986-1997.

"ChemDraw Chemical Structure Drawing Standard" *User's Guide.* CS ChemDraw Pro Version 4.0 for Microsoft Windows and Apple Macintosh. CambridgeSoft Corporation. 1986-1996.

"CSC ChemDraw™ Chemical Structure Drawing Standard" *User's Guide.* CSC ChemDraw and CSC ChemDraw Plus Version 3.0 for Apple Macintosh. Cambridge Scientific Computing, Inc. 1986-1992.

Rubenstein, Stewart. "ChemDraw™ Professional Desktop Publishing for Chemists" Version 2.0 Cambridge Scientific Computing, Inc. 1985-1988.

CS Chemfinder, "The ChemFinder WebServer: Indexing Chemical Data on the Internet", http://web.archive.org.web/19990417145549/chemfinder.camsoft.com/chimia.html, Sep. 16, 2006, 12 pages.

Gelin, B. R. et al., "Inventory Tracking and ChemOffice: CIS Pro Chemical Inventory Package Connects with CS ChemOffice," CambridgeSoft News, Press Release, Aug. 24, 1998, 2 pages.

Gelin, B. R. et al., "ChemACX Chemical Database: Search Over 100 Leading Catalogs on your Desktop or on the WWW," CambridgeSoft News, Press Release, Jan. 18, 1999, 3 pages.

Gelin, B.R., "CS Cheminfo WebServer: Subscription Services Offer WWW Substructure Searching," CambridgeSoft News, Press Release, Aug. 24, 1998, 2 pages.

Anonymous, "Databases Added to ChemWeb", *Information Today*, 2 pages, May 1998.

Barnard, J.M., "Substructure Searching Methods: Old and New", *J. Chem. Inf. Comput. Sci.*, vol. 33, pp. 532-538, 1993.

Brecher, The ChemFlnder WebServer: Indexing Chemical Data on the Internet:, *CHIMIA*, vol. 52, pp. 658-661, 1998.

Business Editors/Health & Medical Writers, "Janssen Selects MDL's ISIS, Relational Chemical Gateway as Informatics Foundation for High Throughout Discovery", 3 pages, Dec. 2, 1998.

Cash, "A Simple Means of Computing the Kekule Structure Count for Toroidal Polyhex Fullerenes", *J. Chem. Inf. Comput. Sci.*, vol. 38, No. 1, pp. 58-61, 1998.

Cambridge Scientific Computing, Inc., "Chem3D the Molecular Modeling System", pp. 1-337, 1990.

Chemlnovation Software, "Chemistry 4-D Draw", *User's Guide*, pp. 1-61, 1997.

Cooke-Fox et al., "Computer Translation of IUPAC Systematic Organic Chemical Nomenclature. 1.Introduction and Background to a Grammar-Based Approach", *J. Chem. Inf. Comput. Sci.*, vol. 29, pp. 101-105, 1989.

Cooke-Fox et al.. "Computer Translation of of IUPAC Systematic Organic Chemical Nomenclature.2.Development of a Formal Grammar", *J. Chem. Inf. Comput. Sci..*, vol. 29, pp. 106-112, 1989.

Cooke-Fox et al., "Computer Translation of IUPAC Systematic Organic Chemical Nomenclature.3.Syntax Analysis and Semantic Processing", *J. Chem. Inf. Comput. Sci.*, vol. 29. pp. 112-118, 1989.

Cooke-Fox et al., "Computer Translation of IUPAC Systematic Organic Chemical Nomenclature.4.Concise Connection Tables to Structure Diagrams", *J. Chem. Inf. Comput. Sci.*, vol. 30, pp. 122-127. 1990.

Cooke-Fox et al., "Computer Translation of IUPAC SYstematic Organic Chemical Nomenclature.5.Steroid Nomenclature", *J. Chem. ma. Comput. Sc.*, vol. 30, pp. 128-132, 1990.

Cooke-Fox et al., "From names to diagrams - by computer", *Chemistry in Britain*, pp. 467-471, 1985.

CRC Handbook of Chemistry and Physics, Student Edition, 76th Edition, Section 2. pp. 2-22 through 2-26, 1996-1996.

Glendening et al., "Natural Resonance Theory: I. General Formalism", *Journal of Computational Chemistry*, vol. 19, No. 6, pp. 593-609, Apr. 30, 1998.

Graovac et al., "Kekule Index for Valence Bond Structures of Conjugated Polycyclic Systems", *Journal of the American Chemical Society*, vol. 95, No. 19, pp. 6267-6273, 1973.

Ihlenfeldt, W.W. et al., "Augmenting Connectivity Information by Compound Name Parsing: Automatic Assignment of Stereochemistry and Isotope Labeling", *J. Chem. Inf. Comput. Sci.*, vol. 35, pp. 663-674, 1995.

Ihlenfeldt, W.D. et al., "Beyond the Hyperative Molecule: Search, Salvage and Visualization of Chemical Information from the Internt", *Pacific Symposium on Biocomputing '96*, vol. SYMP.1, pp. 384-398, Jan. 3, 1996.

Information Today, "ISI develops electronic Index Chemicus", Medford, vol. 10, Iss. 5, p. 64, May 1993.

Kirby et al., "Computer Translation of IUPAC Systematic Organic Chemical Nomenclature. 6. (Semi) Automatic Name Correction", *J. Chem. Int Comput. Sci.*, vol. 31, pp. 153-160, 1991.

Morikawa, "Enumeration of Kekule Structures in Polyradical Polyhexes", *Computers Chem.*, vol. 20, No. 2, pp. 159-165, 1996.

Morrison et al., "Structure and Properties", *Organic Chemistry, Third Edition*, pp. 4-8, Copyright 1973.

Morrison et al., *Organic Chemistry, Third Edition*, p. 324, Copyright 1973.

Notess, G.R., "Offspring of PACS: Local databases on the net", *Database, Weston*, 4 pages, Jun. 1993.

PR Newswire: Judy Hunter, "CAS and Dialog agree to publish new standard", New York, Sec. 1, p. 1 (2 pages total), Sep. 29, 1994.

PR Newswire, New York, "Fisher Scientific Adopts Standards: New Electronic Commerce Web Site Among the First to Embrace Open Buying on the Internet Standards", 2 pages, Feb. 9, 1998.

Ruiz et al., "Error Detection, Recovery, and Repair in the Translation of Inorganic Nomenclatures. 1. A Study of the Problem", *J. Chem. Inf. Comput. Sci. . . .*, vol. 36, No. 1, pp. 16-24, 1996.

Stillwell, "Computer Translation of Systematic Chemical Nomenclature to Structural Formulas - Steroids", *Journal of Chemical Documentation*, vol. 13, No. 3, pp. 107-109, 1973.

Vander Stouw et al., "Automated Conversion of Chemical Substasnces Names to Atom-Bond Connection Tables", *Journal of Chemical Documentation*, vol. 14, No. 4, pp. 185-193, 1974.

Vander Stouw et al., "Procedures for Converting. Systematic Names of Organic Compounds into Atom-Bond Connection Tables", *Journal of Chemical Documentation*, vol. 7, No. 3, pp. 165-169, 1967.

Wilder, "Net Catalog Sales", *Information Week; Manhassete*, 2 pages, Feb. 1, 1999.

Balasubramanian, K.J., "Computer Perception of Molecular Symmetry", *J. Chem. Inf. Comput. Sci.*, vol. 35, pp. 761-770, 1995.

Balducci, R. et al., "Efficient Exact Solution of the Ring Perception Problem", *J. Chem. Inf. Conut. Sci.*, vol. 34, pp. 822-831, 1994.

Bauer, J. et al., "IGOR and RAIN - The First Mathematically Based Multi-Purpose Problem-Solving Computer Programs for Chemistry and Their Use as Generators of Constitutional Formulas", *Informal Commun. Math. Chem. (MATCH)*, No. 27, pp. 31-47, 1992.

Bayada, D.M. et al., "An Algorithm for the Multiple Common Subgraph Problem", *J. Chem. Inf. Comput. Sci.*, vol. 32, pp. 680-685, 1992.

Benecke, C. et al., "MOLGEN, a generator of connectivity isomers and stereoisomers for molecular structure elucidation", *Anal. Chim. Acta*, vol. 314, pp. 141-147, 1995.

Bertrand, A. et al., "DESMOL: a Subroutine for the Generation of Molecular Structures with Stereochemical Information from Connectivity Data", *J. Chem. Res. (S)*, p. 158, 1994.

Bley, K. et al., "Constitutional Formulae generated from Connectivity Information: the Program MDRAW", *J. Chem. Res. (S)*, p. 261 1991.

Carhart, R.E., "A Model-Based Approach to the Teletype Printing of Chemical Structures", *J. Chem. Inf. Comput. Sci.*, vol. 16, No. 2, pp. 82-88, 1976.

ChemDraw Chemical Structure Drawing Standard, *User's Guide*, CS Chem3D 4.0 for Windows and MacIntosh, CambridgeSoft Corporation, 1986-1997.

Dalby, J. et al., "Description of Several Chemical Structure File Formats Used by Computer Programs Developced at Molecuar Design Limited", *J. Chem. Inf. Comput. Sci.*, vol. 32, pp. 244-255, 1992.

Dittmar, P.G. et al., "An Algorithmic Computer Graphics Program for Generating Chemical Structure Diagrams", *J. Chem. Inf. Comput. Sci.*, vol. 17, No. 3, pp. 186-192, 1977.

Downs, G.M. et al., "Review of Ring Perception Algorithms for Chemical Graphs", *J. Chem. Inf. Comput. Sci.*, vol. 29, pp. 172-187, 1989.

Figueras, J. et al., "Automorphism and Equivalence Classes", *J. Chem. Inf. Comput. Sci.*, vol. 32, pp. 153-157, 1992.

Figueras, J., "Ring Perception Using Breadth-First Search", *J. Chem. Inf. Comput. Sci.*, vol. 36, p. 986-991, 1996.

Gothe, S.A. et al., "Computer-Assisted Mechanistic Evaluation of Organic Reactions. 22. The Generation and Use of Three-Dimensional Structures", *J. Org. Chem.*, vol. 58, pp. 5081-5094, 1993.

Helson, "Structure Diagram Generation", *Reviews in Computational Chemistry*, vol. 13, Ch. 6, pp. 313-398, 1999, p. 386 missing.

Judson, R., "Genetic Algorithms and Their Use in Chemistry", Reviews of Computational Chemistry, Ch. 1, vol. 10, pp. 1-73, 1997.

Lieth, C.v.d. et al., "RINGS - a general program to build ring systems", *J. Mol. Graphics*, vol. 2, pp. 117-123, 1984.

Molchanova, M.S. et al., "Computer Generation of Molecular Structures by the SMOG Program", *J. Chem. Inf. Comput. Sci.*, vol. 36, pp. 888-899, 1996.

Rayner, J.D. et al., "A Concise Connection Table Based on Systematic Nomenclatural Terms", *J. Mol. Graphics*, vol. 1, pp. 108-111, 1983.

Rusinko, A. et al., "Using CONCORD to Construct a Large Database of Three-Dimensional Coordinates from Connection Tables", *J. Chem. Inf. Comput. Sci.*, vol. 29, p. 251-255, 1989.

Sadowski, J. et al., "Comparison of Automatic Three-Dimensional Model Builders Using 639 X-ray Structures", *J. Chem. Inf. Comput. Sci.*, vol. 34, p. 1000-1008, 1995.

Shelley, C.A., "Heuristic Approach for Displaying Chemical Structures", *J. Chem. Inf. Comput. Sci.*, vol. 23, pp. 61-65, 1983.

Shmueli, U., "Simple and efficient approach to preparation of molecular drawings", *J. Mol. Graphics*, vol. 2, pp. 111-112, 1984.

Thomson, L.G. et al., "Organic Search and Display Using a Connectivity Matrix Derived from Wiswesser Notation", *J. Chem. Doc.*, vol. 7, pp. 204-209, Nov. 1967.

Weininger, D., "SMILES, a Chemical Language and Information System. 1. Introduction to Methodology and Encoding Rules", *J. Chem. Inf. Comput. Sci.*, vol. 28, pp. 31-36, 1988.

Weininger, D., "Smiles. 3. Depict. Graphical Depiction of Chemical Structures", *J. Chem. Inf. Comput. Sci.*, vol. 30, pp. 237-243, 1990.

Wipke, T., "AIMB: Analogy and Intelligence in Model Building. System Description and Performance Characteristics", *Computer Representation and Manipulation of Chemical Information*, pp. 147-174, Wipke et al. editors, Krieger, NY, 1981.

Wipke, W. T. et al., "Computer-Assisted Three-Dimensional Synthetic Analysis", *Tet. Comput. Method.*, vol. 1, pp. 147-174, 1988.

Zimmerman, B.L., Thesis, University of Pennsylvania, 1971.

Zipple, M. et al., "Spektren - A Computer System for the Identification and Structure Elucidation of Organic Compounds", *Anal. Chim Acta*, vol. 140, pp. 123-142, 1982.

* cited by examiner

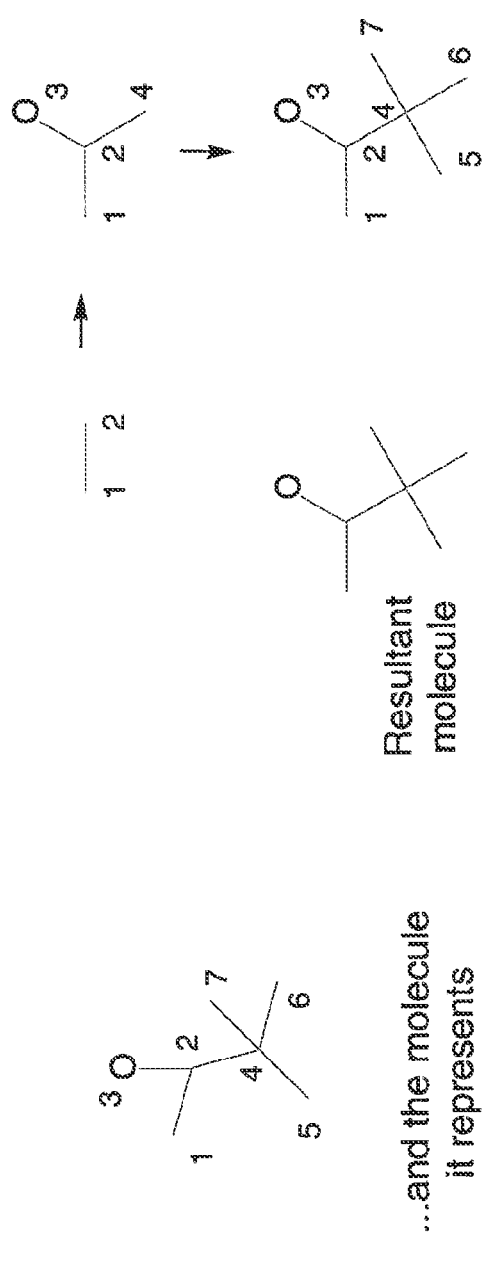
FIG. 1C
Resultant molecule
...and the molecule it represents
FIG. 1B
(Prior Art)
Simplified Connection Table
FIG. 1A
(Prior Art)
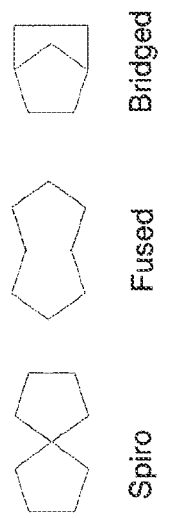 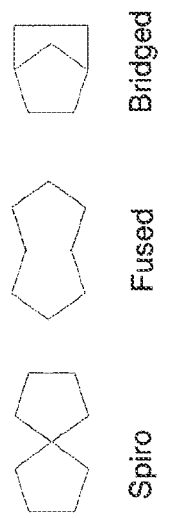 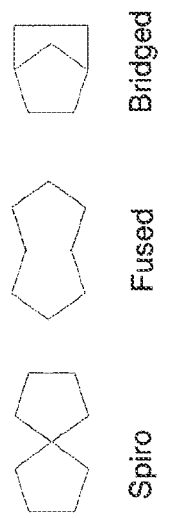 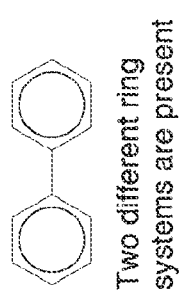
Spiro  Fused  Bridged
Two different ring systems are present
FIG. 2
(Prior Art)

a. Given structure (Starting coordinates are irrelevant.)

b. Perceived symmetry. Like letters indicate equivalent atoms or bonds. Symmetry is three-fold.

c. The pivot atom is taken as the first seed atom.

d. Place an adjacent atom.

e. Place equivalent atoms, with three-fold symmetry

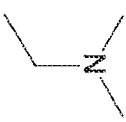
f. Place next atom. (Direction is arbitrary.)

g. Place equivalent atoms, with three-fold symmetry.

FIG. 4

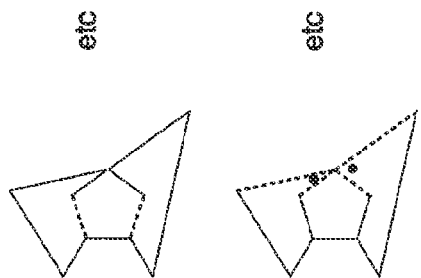
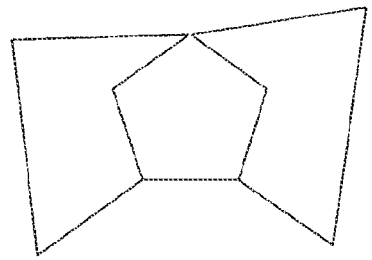
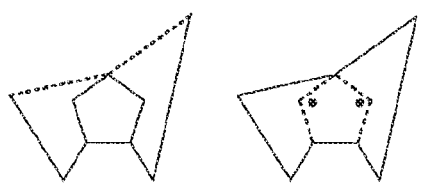
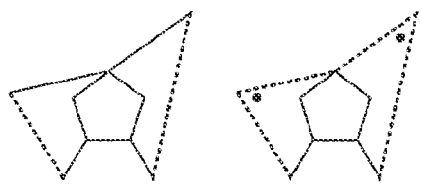
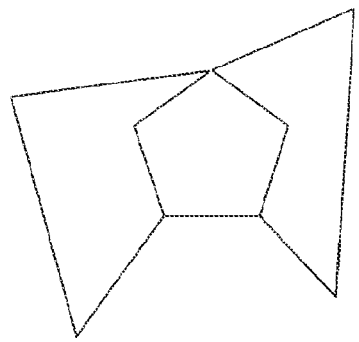
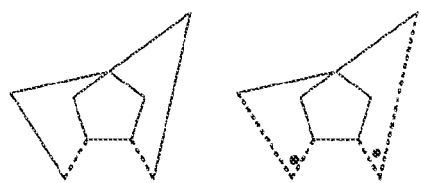
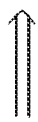
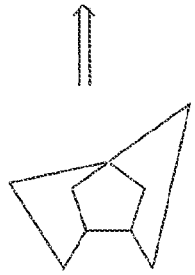
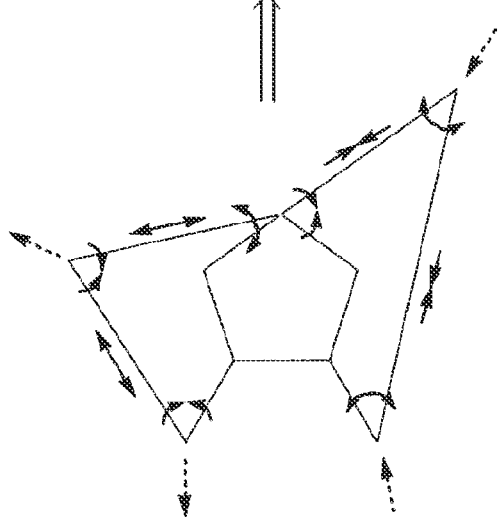
FIG. 6
FIG. 7

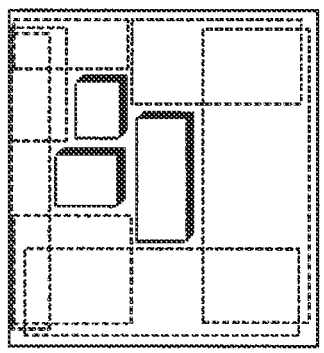
d. After imprinting the third box, there are eight free rectangles. (Translation step not included for clarity.)
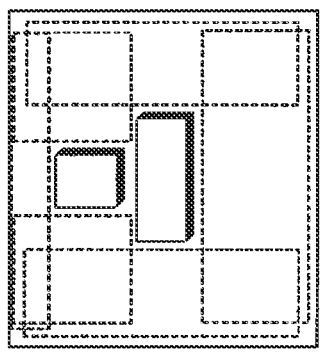
c. After imprinting the second box, there are seven free rectangles. (Translation step not included for clarity.)
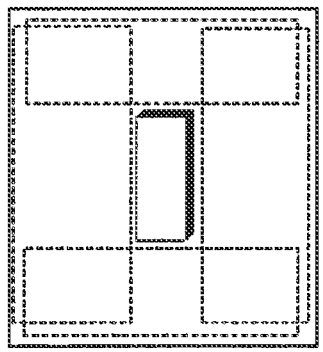
b. After imprinting the first box, there are four free rectangles.
a. Initial free rectangle
FIG. 12

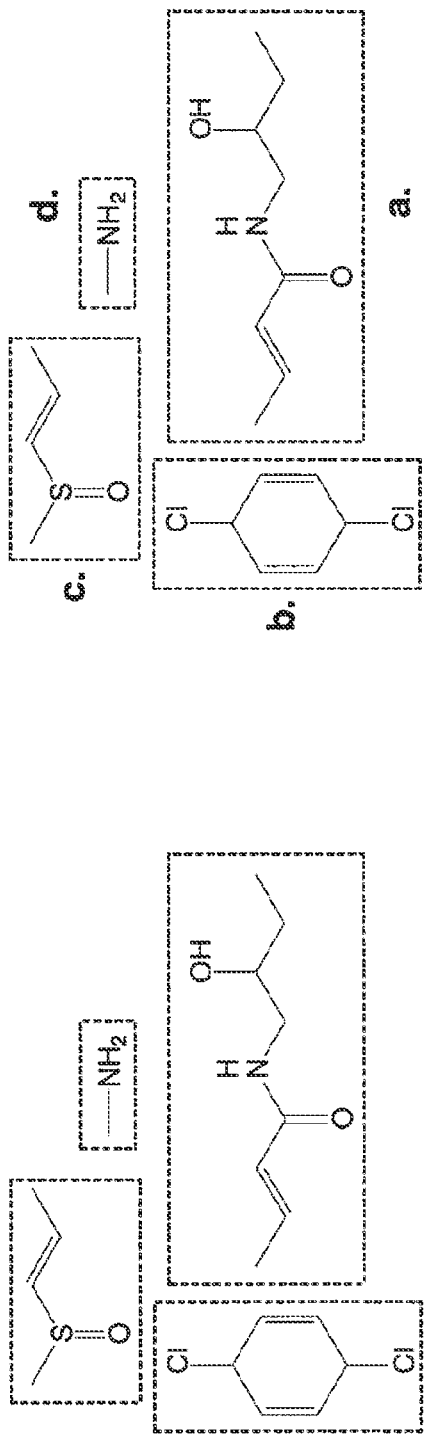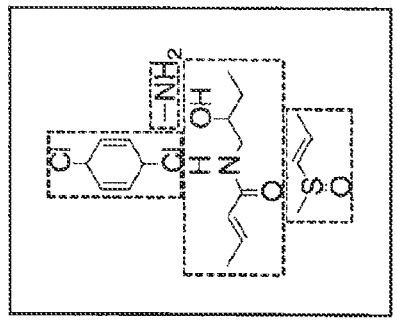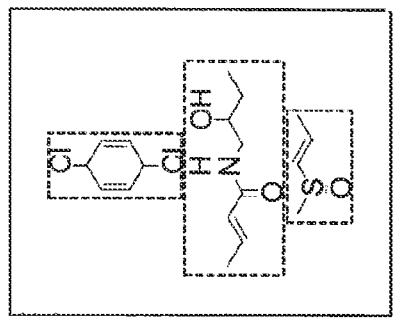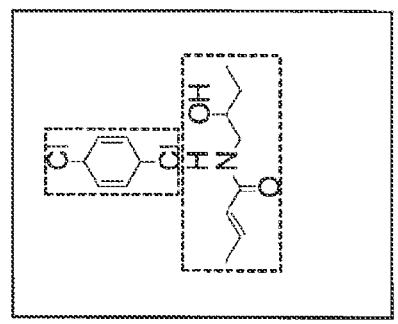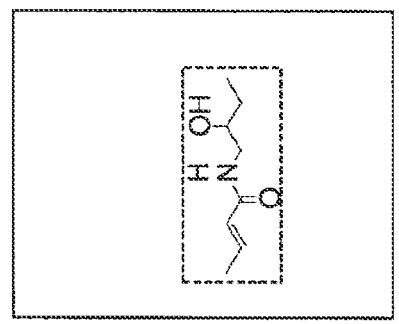
FIG. 13

ENHANCING STRUCTURE DIAGRAM GENERATION THROUGH USE OF SYMMETRY

CROSS-REFERENCE TO RELATED APPLICATIONS

This application claims the benefit of U.S. Provisional Application Ser. No. 60/119,654 entitled STRUCTURE DIAGRAM GENERATION filed on Feb. 11, 1999, incorporated herein.

REFERENCE TO SOURCE CODE APPENDIX

A Microfiche Source Code Appendix forms part of this application. The appendix, which includes a source code listing relating to an embodiment of the invention, includes 33 frames on 1 sheet of microfiche.

This patent document (including the source code appendix) contains material that is subject to copyright protection. The copyright owner has no objection to the facsimile reproduction by anyone of the patent document as it appears in the Patent and Trademark Office file or records, but otherwise reserves all copyright rights whatsoever.

BACKGROUND OF THE INVENTION

This application relates to enhancing structure diagram generation.

A molecule is typically represented in a computer by a connection table that identifies atoms in the molecule and specifies connections ("bonds") among the identified atoms. The connection table may also describe associated properties such as atom type, bond order, charge, and stereochemistry. A diagrammatic representation of the molecule may be derived from the connection table. Examples of a connection table and a corresponding diagram are illustrated in FIGS. 1A–1B (for clarity, hydrogen atoms are not shown).

In chemistry, with reference to FIG. 2, a chain of atoms that closes on itself is known as a ring. In the context of a ring or a ring system (see below), a bridge is a chain of atoms that begins at an origin point (which is an atom) in the ring or system, and connects back to the same ring or system at least two atoms away from the origin point, to form an additional ring. A chain that reconnects at the same origin point instead is known as "spiro". A chain that reconnects to an atom that is adjacent to the origin point is known as "fused".

A ring system, which is also known as a "cyclic system", is a group of rings such that (1) each ring shares one or more bonds with another ring in the group and (2) the group cannot be divided into smaller cyclic systems. An arrangement in which two rings are connected by a linking, non-cyclic ("acyclic") bond is considered to include two cyclic systems, not one. As used herein, "ring system" has a meaning consistent with an understanding that a spiro ring includes two distinct ring systems.

SUMMARY OF THE INVENTION

A method and a system are provided for enhancing structure diagram generation ("SDG"). In SDG, aesthetic two-dimensional ("2-D") coordinates for use in a diagrammatic representation ("diagram") of a molecule are derived from a connection table for the molecule. SDG may also improve the aesthetic qualities of a chemical structure diagram having existing coordinates, if available. SDG is enhanced by expressing the symmetry present in the molecule, by making use of symmetry in the 2-D dynamics used to lay out rings and chains, by construction of bridges using an open polygon method together with a potential function, and by an elegant approach to the relative positioning of molecules ("free rectangle method").

Other features and advantages will become apparent from the following description, including the drawings, and from the claims.

BRIEF DESCRIPTION OF THE DRAWINGS

FIG. 1A is an illustration of computer data.

FIGS. 1B–1C, 3–4, 6–13 are illustrations of output produced by software.

FIG. 2 is an illustration of chemical structures.

DETAILED DESCRIPTION

Figure 3:
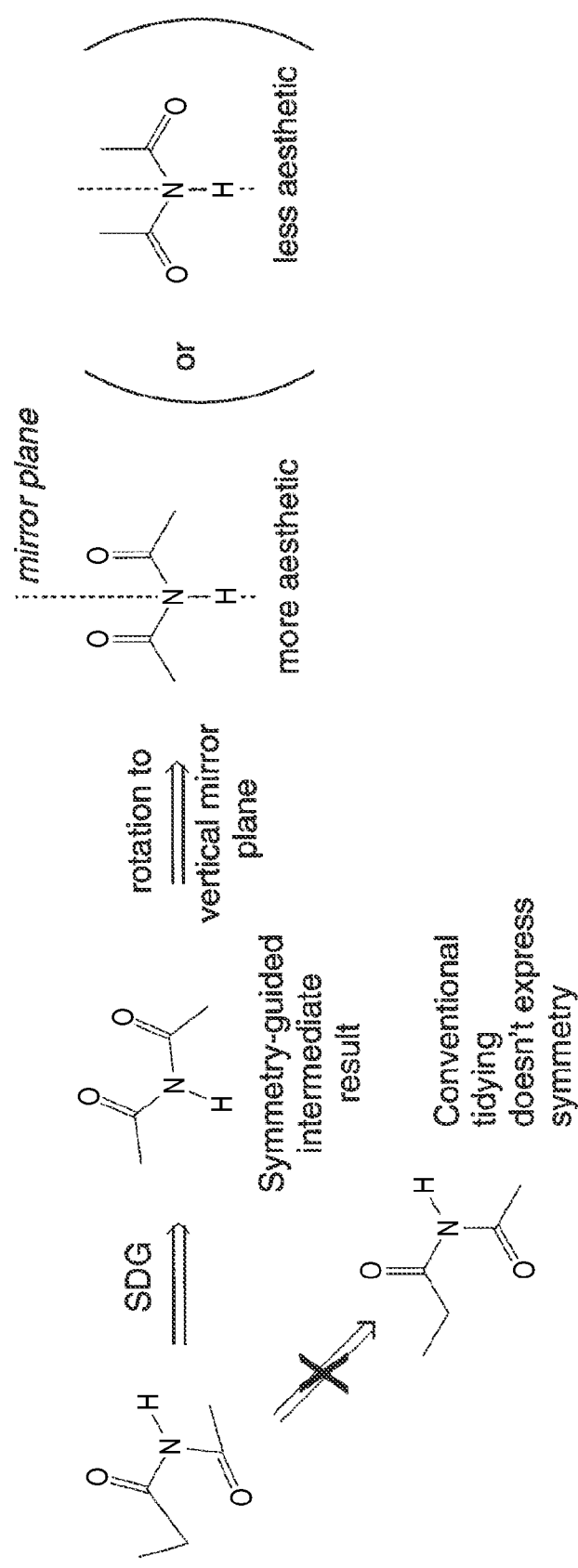

Structure diagram generation ("SDG") is a process in which two dimensional ("2-D") coordinates are derived from a connection table for a structure, allowing a diagram of the molecule to be displayed or printed. SDG is described in detail in H. E. Helson, "Structure Diagram Generation", in "Reviews in Computational Chemistry", K. B. Lipkowitz and D. B. Boyd, Eds., Wiley-VCH, New York, 1999, Vol. 13, at 313–398, which is incorporated herein. This application is filed simultaneously with a United States patent application entitled DERIVING CHEMICAL STRUCTURAL INFORMATION, Ser. No. 09/502,810 filed Feb. 11, 2000, which is incorporated herein.

Current methods include a less refined implementation of SDG. For example, earlier versions of CambridgeSoft Corporation's ChemDraw® program employed a feature that allowed users to regularize bond lengths and angles, and lay out ring systems. ChemDraw®, however, did not consult symmetry when creating two-dimensional organic structures, was unable to satisfactorily fabricate bridges, and lacked the ability to inter-position molecules. Although other methods of chemical structure generation have employed different methodologies, they suffered the same shortcomings, and there was no consideration in these methods for symmetry. Thus, there have been problems associated in the art with the creation of two-dimensional organic structures.

The present invention provides new methods of SDG. The new methods enhance SDG by improving the layout of chemical structure diagrams. The enhanced SDG provides users the ability to more quickly recognize chemical molecules. The enhanced SDG also allows users to more quickly recognize important features of chemical molecules, such as symmetry. As a result of the methods of the invention, the enhanced SDG methods are also useful for purposes of publication. In addition, the methods provide users the ability to improve chemical structure diagrams quickly and efficiently, thus avoiding tedious manipulation.

In SDG, the two-dimensional coordinates may be derived with or without preexisting coordinates. Cases without preexisting coordinates ("de novo" cases) are common and include chemical name translation, isomer enumeration, translation from a linear notation such as SMILES, nickname/superatom expansion, and automated structure elucidation.

In cases in which preexisting coordinates are available ("structure cleanup" cases), it may be possible to improve a structure diagram while preserving some or all existing stylistic choices. For example, if a structure diagram is drawn with or imported into a structure drawing program, the program may be directed to "clean up" undesirable aspects of the structure diagram. In another example, diagram improvements may be needed in the case of a synthesis planning program, in which structure diagrams are generally well drawn but may have had bonds broken and reformed in awkward locations.

SDG may also be needed in conversions of structure diagrams from three-dimensional ("3-D") to 2-D. In at least some cases, structure diagrams that are stored and manipulated in a 3-D form may be converted to 2-D diagrams upon display to make the structure diagrams more easily recognizable to human users.

As a result, a connection table to which SDG is applied may have 2-D or 3-D coordinates or may lack coordinates.

SDG includes at least four possible stages ("phases"): perception, pre-assembly analysis, assembly, and post-assembly. The pre-assembly phase, if applicable, may include deriving a feature such as the shape of a ring system that is subsequently attached whole to an acyclic portion in the assembly phase. In the assembly phase, the neighbors of an atom that has been positioned (a "seed" atom) are each examined in turn, and are positioned at respective aesthetic angles and distances from the seed atom. FIGS. 1A–1C illustrate an example. A connection table of a simple molecule (FIG. 1B) is shown in FIG. 1A. In a specific embodiment, one of the atoms is arbitrarily chosen as a first seed atom. The neighbors of the first seed atom are positioned; each of the neighbors in turn takes the role of the seed atom in subsequent iterations, until all of the atoms are positioned, as shown in FIG. 1C for the connection table of FIG. 1A.

SDG is enhanced as described below.

In a first aspect of the enhancement, symmetry is used in the assembly phase, i.e., for general layout. Chemical structure diagrams that express molecular symmetry facilitate human interpretation of the chemical structures that are represented. For example, the presence of symmetry provides clues for the molecular substance's synthesis. Symmetry affects the substance's physical properties (particularly those affected by entropy), such as melting and boiling points, and heat of vaporization. Symmetry can affect the substance's light-bending properties. In particular, a substance that has a plane of symmetry is not "optically active". In general, since the human eye tends to recognize symmetry quickly, a diagram that expresses a molecule's symmetry allows the symmetrical characteristics of the molecule to be rapidly perceived by a human viewer.

According to the enhancement, when a diagram is to be produced for a molecule, symmetry inherent in the molecule is perceived, and during layout of the structure diagram, representations of atoms and bonds are positioned to express the perceived symmetry. In a specific implementation, a plane of symmetry (also known as a mirror plane) perceived in a molecule is expressed vertically or horizontally (see FIG. 3).

Figure 14:
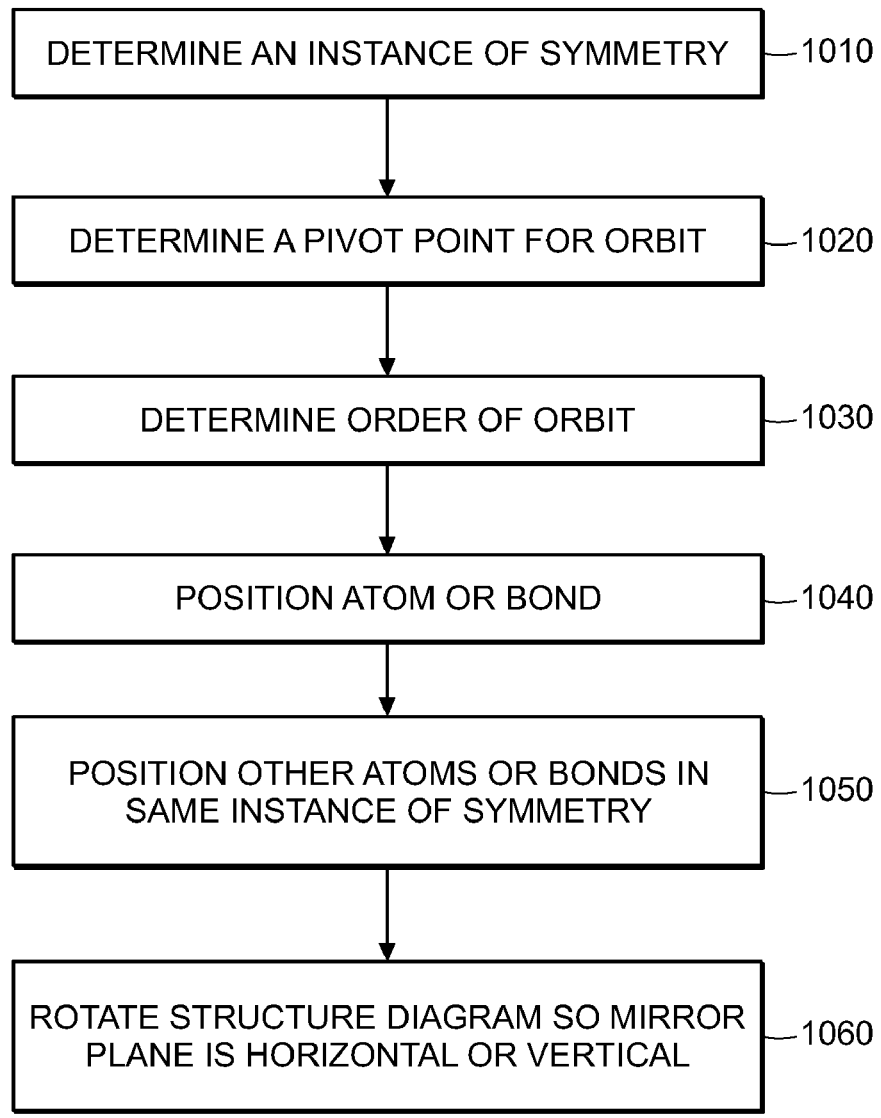

In a first step in using symmetry in general layout (see FIGS. 4 and 14), an instance of symmetry is determined (step 1010). Detection of symmetry is described in M. Razinger, K. Balasubramanian, and M. E. Munk, "Graph Automorphism Perception Algorithms in Computer-Enhanced Structure Elucidation", *J. Chem. Inf. Comput. Sci.*, 33, 197 (1993). The instance of symmetry may be based on one or more of rotation, reflection (see b. in FIG. 4), inversion, and translation, and may or may not take stereochemistry into account. A particularly effective combination in the determination is an instance of symmetry based on rotation and reflection, and a flexible incorporation of stereochemistry. If a full consideration of stereochemistry does not reveal an instance of symmetry, a partial consideration of stereochemistry, e.g., of double bond stereochemistry only, is employed. The instance of symmetry is here represented as a list of orbits, i.e., a list of groups of equivalent atoms and bonds.

Additionally, a "pivot" point is determined for each orbit (step 1020). The pivot point is determined to be the one or more atoms or bonds that resides at the graph-theoretic center of the atoms and bonds in the orbit, i.e., those atoms (bonds) having the smallest value of the largest graph-theoretic distance to any other atom (bond) in the orbit. The graph-theoretic distance between two atoms (bonds) is equal to the number of bonds (atoms) in the shortest path between them. For example, in FIGS. 3–4, the nitrogen atom is determined to be the pivot point; in n-butane, the central bond is determined to be the pivot point, and in 1,2,3-trimethylcyclopropane, all cyclic atoms and bonds are determined to be the pivot point.

The "order" of each orbit for each instance of symmetry is also determined (step 1030). The order indicates whether the instance corresponds to a two-fold rotation, a three-fold rotation, a four-fold rotation, and so on, or a reflection. In cases in which the symmetry of an orbit includes both reflection and an N-fold rotation, N being greater than 2, it is advantageous to treat the instance as having an order indicating that the instance corresponds to the N-fold rotation. Thus, rotational symmetry takes priority over reflection if the associated rotation is at least three-fold.

Figure 5:
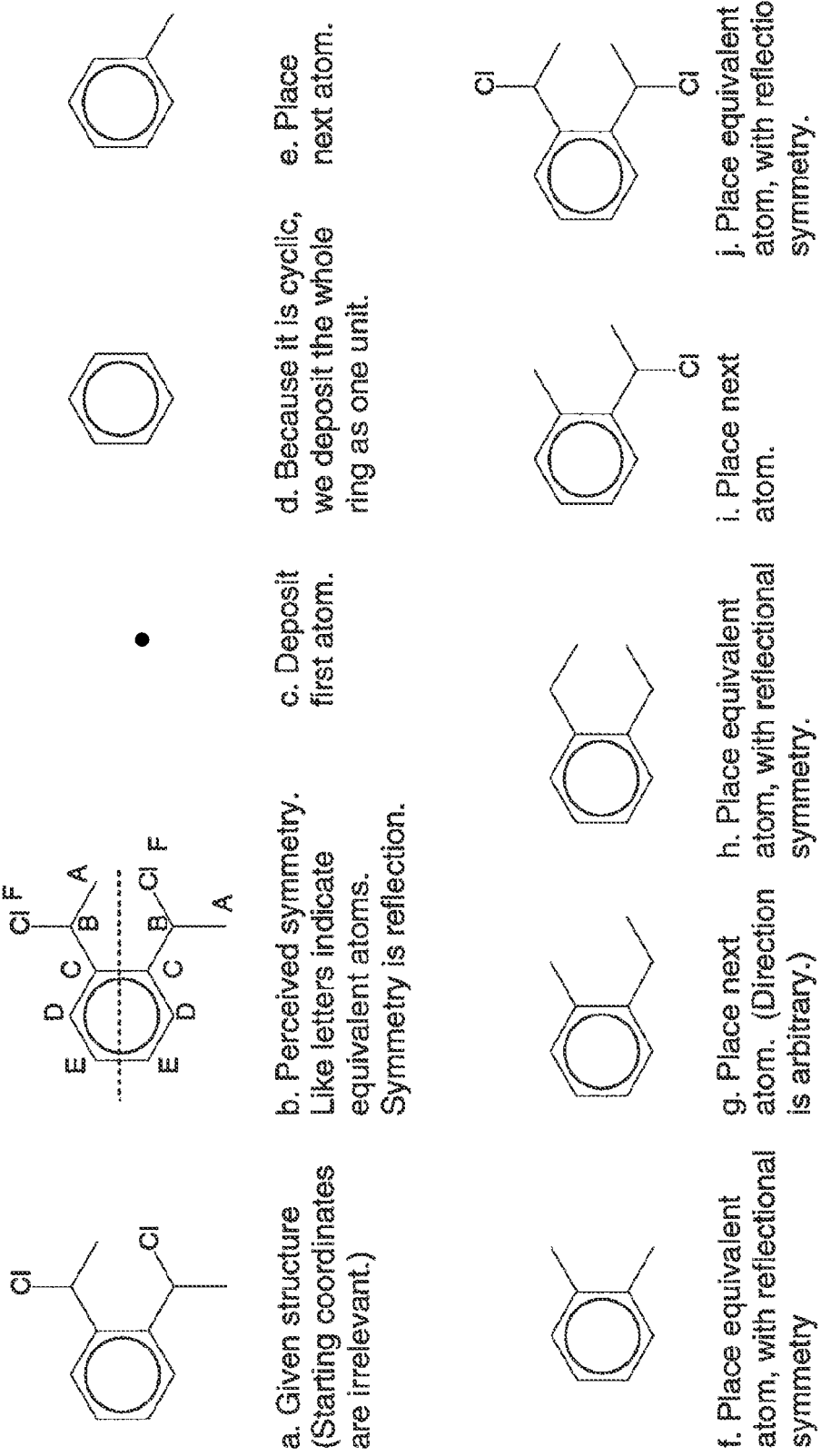
FIGS. 5, 14–16 are flow diagrams of computer-based procedures.

When an atom or bond is positioned during the assembly phase (step 1040) (see FIGS. 1, 4), attention is paid to whether the atom or bond belongs to one of the determined instances of symmetry. In a case in which the atom or bond so belongs, after the atom or bond is positioned, other atoms or bonds, respectively, that belong to the same instance are positioned immediately thereafter (step 1050) (see FIGS. 4–5). If the type of symmetry involved is reflection (see FIG. 5), the other atom or bond is placed on the opposite side of the mirror line that runs through the pivot point of the group in the instance. In such cases, the direction may be arbitrary if only two atoms have been placed. If the type of symmetry involved is rotation, the symmetrically equivalent atoms or bonds are positioned at appropriate rotational points, based on the pivot point. First positioning an atom or bond that represents the pivot point facilitates symmetric positioning but is not always possible, such as when multiple regions of independent symmetry are involved (e.g., in an unsymmetrical ether, each end of which is locally symmetric).

After all atoms and bonds have been placed, the structure diagram is rotated so that its mirror plane is horizontal or vertical (step 1060) (see FIG. 3).

In another aspect of the enhancement of SDG, symmetry is used in a "dynamics" method of layout. A 2-D version of molecular dynamics is used in some situations to lay out structure diagrams of molecules in connection with designing new ring systems, improving existing ring systems, or laying out or improving acyclic portions. Such an effort may use a predefined set of optimal bond lengths and angles ("parameters"), or may seek to equalize adjacent lengths and angles. The process is iterative, wherein in each iteration the difference between a current parameter and an optimal parameter is calculated for each atom and bond, and is interpreted as a corrective force on the atom or bond, which affects the position of the atom or bond as submitted to the next iteration. The iterative process continues until the net corrective force on every atom or bond is zero or nearly zero, so that the structure diagram for the molecule is determined to be at equilibrium.

Figure 15:
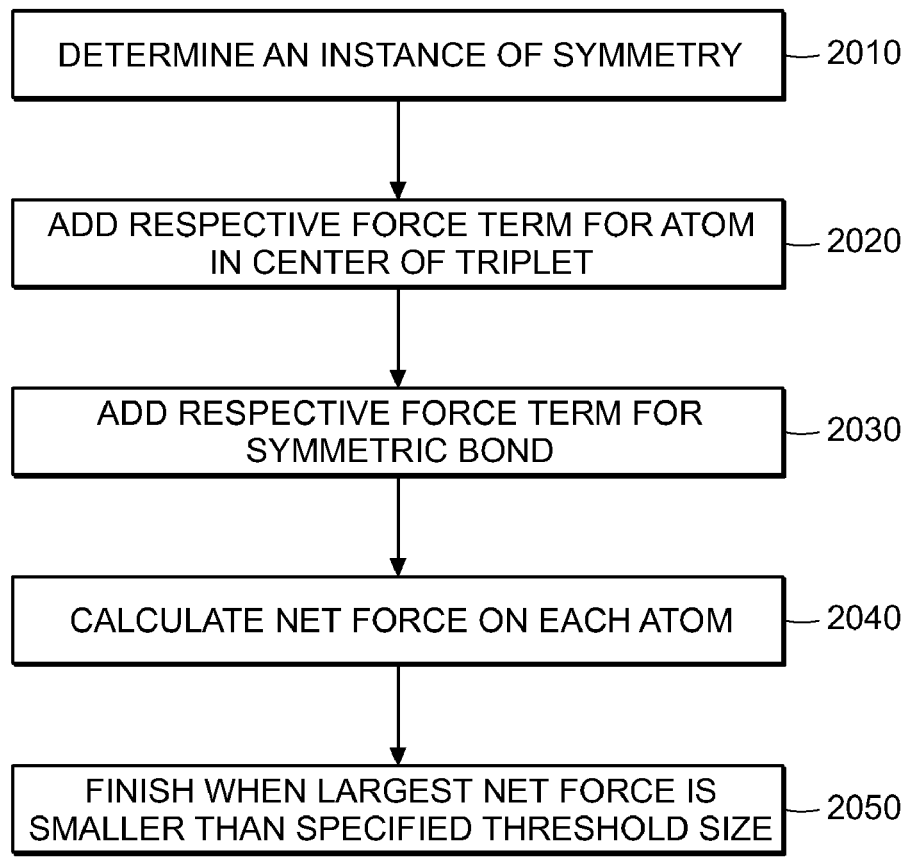

A method of adding symmetry as a parameter in dynamic ring layout is now described (FIG. 15). The concepts presented are also applicable to acyclic systems. Dynamic ring layout in general is described in H. E. Helson, Ph.D., Thesis, "Simulation of Carbene Chemistry and Other Problems in Computer-Assisted Organic Synthesis.", Purdue University, 1993; H. E. Helson and W. L. Jorgensen, J. Chem. Inf. Comput. Sci., 34,962 (1994), "Computer-Assisted Mechanistic Evaluation of Organic Reactions. 25. Structure Diagram Positioning"; and H. E. Helson, "Structure Diagram Generation", in "Reviews in Computational Chemistry", K. B. Lipkowitz and D. B. Boyd, Eds., Wiley-VCH, New York, 1999, Vol. 13, at 313–398. As shown below, a symmetry term is incorporated in a force field, which drives symmetrically equivalent regions in different parts of the structure diagram toward a common appearance. Instances of symmetry are determined (step 2010). The symmetry detection referenced above is an example of such a determination. In a specific implementation, the instances are determined based on rotation and reflection, without regard for bond orders or types, atom characteristics (e.g., mass, type, charge), or acyclic portions, and the determination focuses exclusively on the locations of the bonds. The instances of symmetry may be determined without supplied coordinates. The determination takes double bond isomerism into account: E and Z isomers are recognized as not being equivalent. Specific implementations may also take into account 2-D graphics-based characteristics not normally connected with molecular symmetry, such as bond zig-zags, or whether a bond is "exterior" or "interior", i.e., whether or not the bond has a clear path to the edge of the drawing area.

The instance of symmetry, regardless of character and origin, may be represented in any of several ways. In a specific implementation, the instance is represented by two lists of groups: a list of equivalent triplets of atoms, and a list of equivalent pairs of bonds (see FIG. 6, in which the top and bottom sequences illustrate equivalent bonds and atom triplets, respectively, and each dot marks the central atom in a triplet).

In each iteration for each triplet, a respective force term ("$F_a$") is added for the atom in the center of the triplet (step 2020). An optimal interior angle ("optimal angle") of the triplet of atoms is derived, as the average of the interior angles of all the triplets in an orbit, i.e., in a group of symmetrically equivalent atoms or bonds. $F_a$ is based on, and in a specific implementation is proportional to, the difference between the optimal angle and the current angle. $F_a$ acts along the angle's bisector, in a direction that would bring the angle closer to the optimal angle. $F_a$ may compete with other terms, such as a bond angle term for equalizing adjacent bond angles.

In each iteration, another respective force term ("$F_b$") is added for each symmetric bond (step 2030). $F_b$ has the effect of lengthening or shortening a bond to make the bond's length more similar to the lengths of the other bonds in the orbit. A bond's length is changed by moving the atoms at the bond's endpoints closer together or farther apart. Thus $F_b$ is expressed by treating $F_b$ as a force on each of its two adjacent atoms. $F_b$ may compete with other terms, such as a bond length term for equalizing adjacent bond lengths.

During each iteration, a net force on each atom is calculated, as the sum of the forces including $F_a$ and $F_b$ acting on the atom (step 2040). The position of each atom is moved by an amount proportional to the respective net force. In a specific implementation, the iterative process is determined to be complete when the largest net force to be accounted for in the iteration is smaller than a specified threshold size (step 2050).

FIG. 7 illustrates an example of net forces and the iterative evolution. In FIG. 7, double arrows show the forces due to symmetry on selected atoms and bonds, single dashed arrows represent bond angle forces re-expressed as atom translation, and other forces not related to symmetry are omitted for clarity and to reduce clutter. The rightmost structure diagram in FIG. 7 represents an improvement over the leftmost structure diagram.

Figure 8:
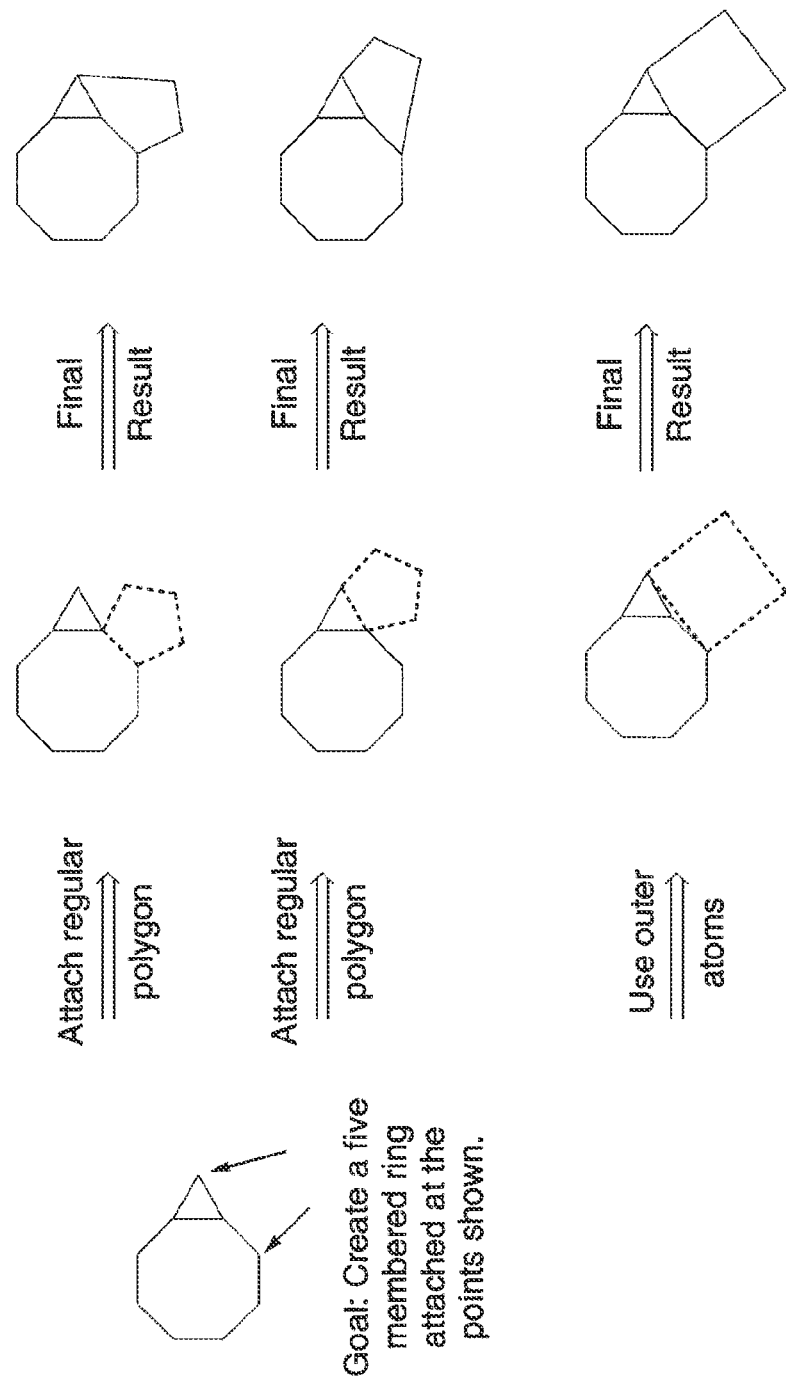

Construction of bridged cyclic systems may involve problems of atom and bond overlap, and irregular angles. In another aspect of the enhancement of SDG, bridges in cyclic systems are constructed using an open polygon method in conjunction with a potential function. In an example illustrated in FIG. 8, SDG has already produced two rings that are part of a tricyclic system. In a regular polygon method, a third ring (indicated by dashed lines in FIG. 8) is attached by constructing the third ring as a regular polygon, so as to fuse the third ring to either one of the rings already produced. In such a case, as shown in the top two example sequences in FIG. 8, uneven coordinates are produced. Alternatively in the regular polygon method, the regular polygon can be attached directly at the two bridgehead atoms, as shown in the bottom example sequence in FIG. 8, but uneven results are still achieved. By contrast, the open polygon method is able to generate evenly spaced coordinates between the two termini where the ring will be attached, as shown in an example sequence in FIG. 9, in which a five-membered ring is fused onto a bicyclo[6.1.0] system. See H. E. Helson, "Structure Diagram Generation", in "Reviews in Computational Chemistry", K. B. Lipkowitz and D. B. Boyd, Eds., Wiley-VCH, New York, 1999, Vol. 13, at 313–398, which is incorporated herein.

Figure 9:
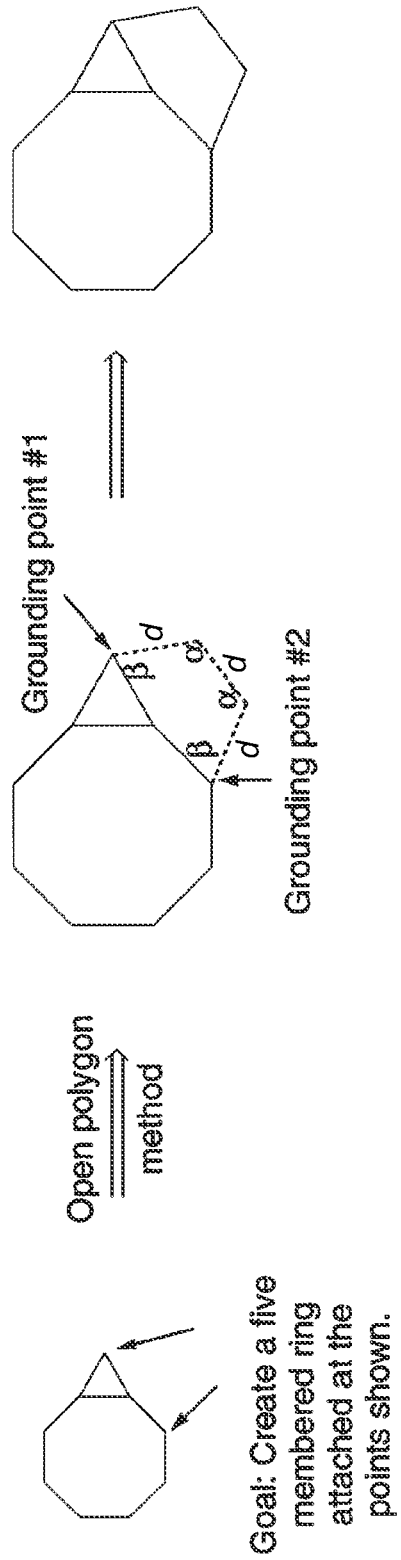

In the open polygon method, coordinates of missing points are derived from two grounding points, the number of missing points, and an optimal bond length ("d"), such that, as shown in FIG. 9, interior angles ("$\beta$") at the two grounding points are equal and the remaining interior bond angles ("$\alpha$") are all equal.

The open polygon method can be used to create bridges. In FIG. 9, the two grounding points correspond to the two bridgehead atoms. In at least some cases, however, the resulting bridge may be determined to be too close or too far away from the base ring skeleton such that the resulting bridge crowds the base ring skeleton. As a result, the circumference of the bridge is varied by varying the value of d in FIG. 9.

Figure 10:
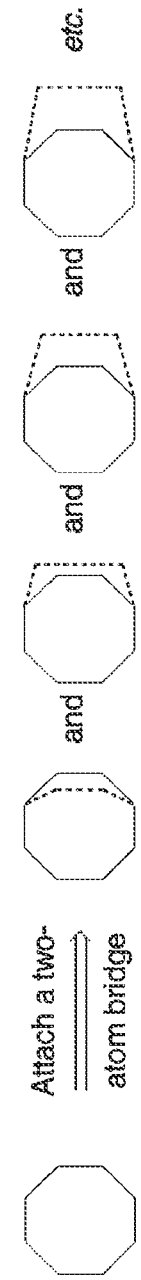

FIG. 10 illustrates an example of an application of the open polygon method to bridge construction. The leftmost structure diagram represents the preexisting ring skeleton to which the bridge will be affixed. The other structure diagrams represent the results of applying the open polygon method using various values of d. The one producing the least congestion, among other factors, is chosen. More specifically, the value of d that is selected is the value that (1) produces the least congestion between the bridge and the base ring skeleton, as measured, for example, by a two-body inverse-distance squared potential function, (2) does not produce near-linear bond angles, i.e., does not produce an a that is nearly 180 degrees, and (3) uses a bond length d that is close to the optimal bond length, as may be expressed in a weighted function, such as:

Rating=$c_1$*Congestion+$c_2$*max (0, (180−$\alpha$)−threshold)+$c_3$*|scale−1.0|

In such a function, $c_1$, $c_2$ and $c_3$ are constants determined in a specific implementation; and scale is the ratio of d to the standard bond length. In a specific implementation, the bond angle term is active only above a certain threshold, such as 120 degrees. The version of the bridge that minimizes the rating is chosen.

Figure 11:
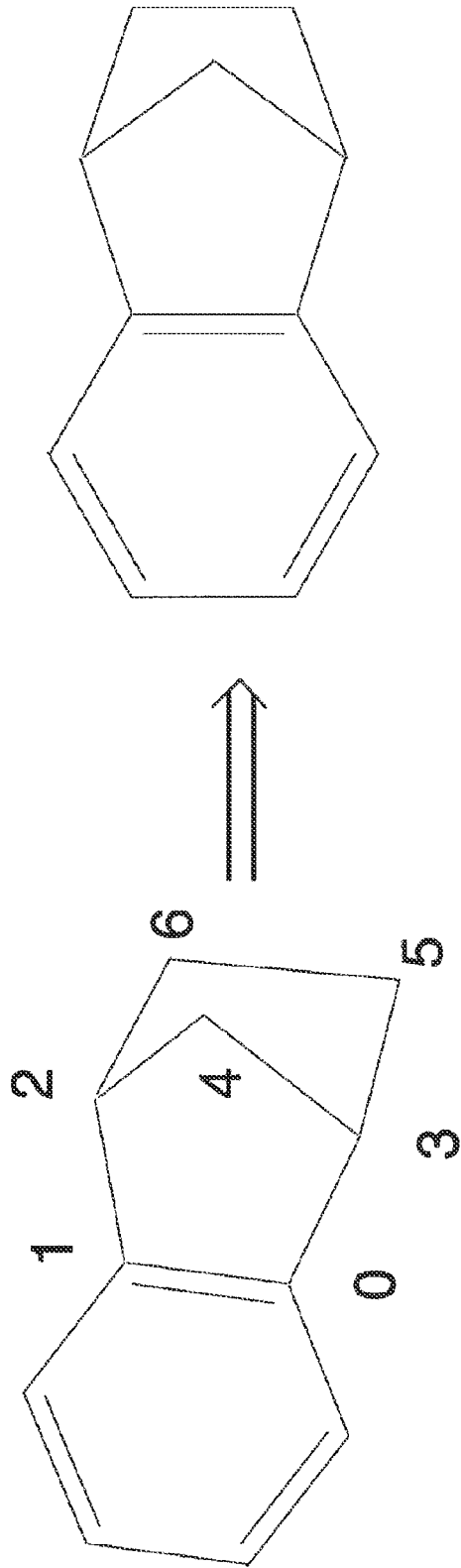

FIG. 11 illustrates an application of the ratings method. Each line starting with "Rating for" indicates a rating computed for a particular bond length. For example, the second such line reports a rating of 313.185 for a bond length scale of 0.5 where the contribution for congestion is 45.185, the contribution for a non-unitary bond length is 40.00, and the contribution for a non-linear bond angle of 177 is 228. With respect to FIG. 11, the bond length scale that achieves the lowest rating and is therefore selected is 1.3.

In another aspect of the enhancement of SDG, a placement procedure is executed to arrange molecule structure diagrams closely together without overlapping. In at least some cases, the procedure is executed as a final step of SDG, after the molecule structure diagrams have been produced individually. The procedure is analytic in that the procedure does not rely on an indefinite number of iterations and is not affected by the starting positions of the components.

Figure 16:
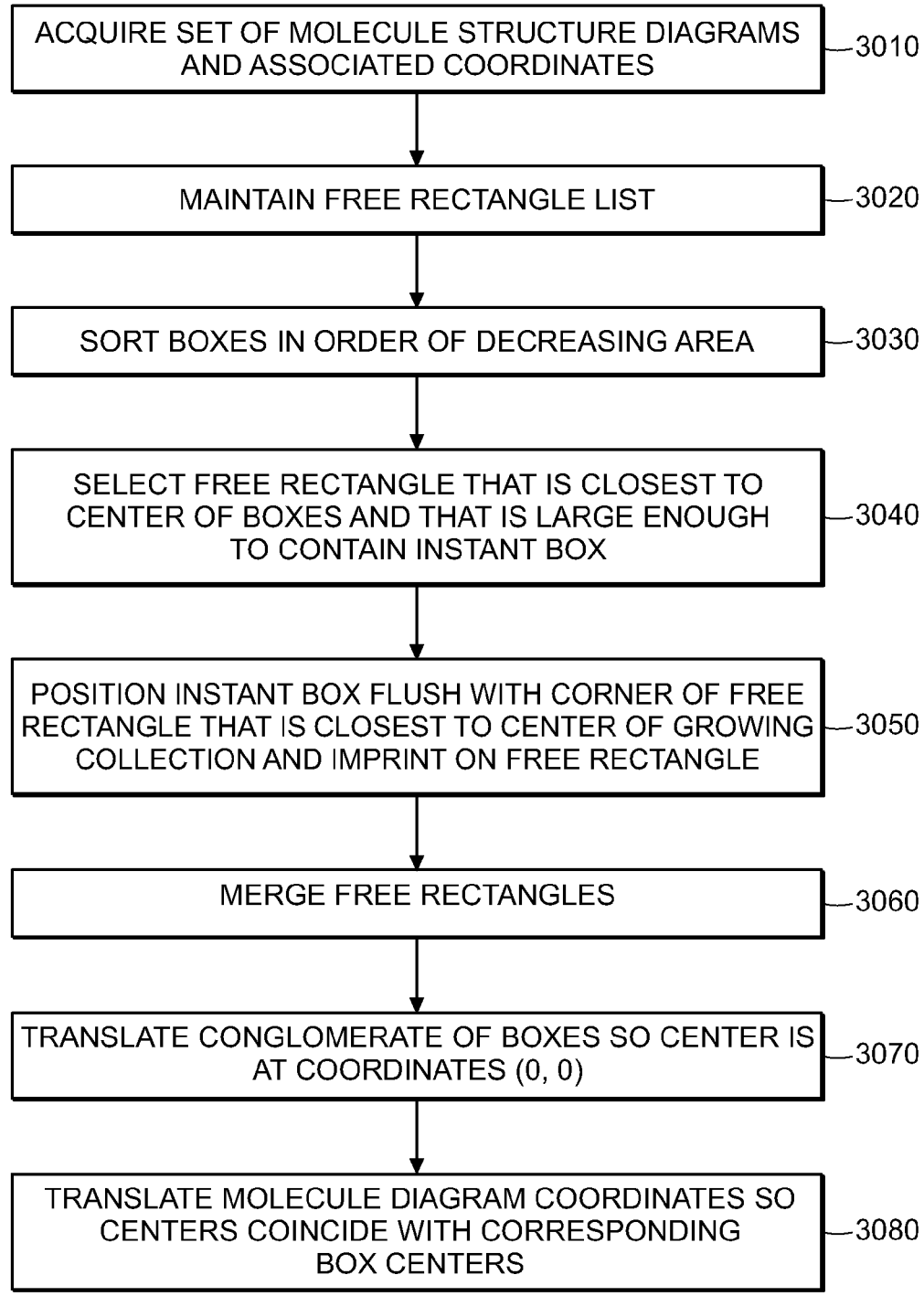

A specific implementation of the procedure is now described (FIG. 16), and an example as described below is illustrated in FIG. 13. A set of molecule structure diagrams and associated coordinates are acquired (step 3010). Each molecule structure diagram is represented by a conceptual box, defined by the structure diagram's smallest enclosing rectangle plus a small margin.

A "free rectangle" list is maintained that keeps track of which areas of the display area are unused (step 3020). The list is initialized to one free rectangle that occupies all of 2-D space and extends from negative infinity to positive infinity in both X and Y dimensions.

The boxes are sorted, and each is treated as follows, in order of decreasing area (step 3030). A free rectangle is selected that is closest to the center of the boxes and that is large enough to contain the instant box (step 3040). The center of a collection ("conglomeration") of boxes is defined as the average of the centers of the boxes weighted by the boxes' respective areas, or, as the center of the smallest rectangle that can enclose the boxes. The instant box is positioned flush with that corner of the free rectangle that is closest to the center of the growing collection (initially at coordinates (0,0)), and is imprinted on the free rectangle (step 3050). In imprinting, the original free rectangle is replaced by zero or more new free rectangles. New free rectangles may be created in the leftover space, i.e., wherever the box does not occlude the original rectangle (see FIG. 12, which illustrates an example of the evolution of free rectangles and box placement). In an analogy in which a cookie cutter represents the box and dough represents the free rectangle, the dough underneath the cutter is discarded and the remaining areas of dough represent the leftover space that becomes the new free rectangles. In at least some cases, the sum of areas is not conserved, because each new free rectangle expands in both X and Y dimensions to the furthest extent possible without penetrating existing boxes. Several overlapping free rectangles may be necessary to fully span the leftover space (see FIG. 12). A free rectangle that could not contain the smallest box is not created.

In a specific implementation, overlapping free rectangles may be merged to help avoid a profusion of inconsequential free rectangles (step 3060). For example, rules may be enforced that dictate that two free rectangles should be merged such that the resulting free rectangle does not extend over any points not contained in either progenitor, provided that the percentage of area lost in the merger is less than a specified size, such as ten percent of the original area.

The conglomerate of boxes is translated so that its center is at coordinates (0,0) (step 3070). The molecule diagram coordinates are translated so that their centers coincide with their corresponding box centers (step 3080).

A practical example of the molecule arrangement procedure is illustrated in FIG. 13. Initially, a collection of molecules is presented to be positioned. Corresponding enclosing boxes are identified in an order of decreasing area (a. to d.), and are positioned one by one in the same order (i.e., a. first, d. last), to produce a space-efficient, non-overlapping arrangement as shown.

All or a portion of the procedures described above may be implemented in hardware or software, or a combination of both. In at least some cases, it is advantageous if the technique is implemented in computer programs executing on one or more programmable computers, such as a personal computer running or able to run an operating system such as UNIX, Linux, Microsoft Windows 95, 98, 2000, or NT, or MacOS, that each include a processor, a storage medium readable by the processor (including volatile and non-volatile memory and/or storage elements), at least one input device such as a keyboard, and at least one output device. Program code is applied to data entered using the input device to perform the technique described above and to generate output information. The output information is applied to one or more output devices such as a display screen of the computer.

In at least some cases, it is advantageous if each program is implemented in a high level procedural or object-oriented programming language such as Perl, C, C++, or Java to communicate with a computer system. However, the programs can be implemented in assembly or machine language, if desired. In any case, the language may be a compiled or interpreted language.

In at least some cases, it is advantageous if each such computer program is stored on a storage medium or device, such as ROM or optical or magnetic disc, that is readable by a general or special purpose programmable computer for configuring and operating the computer when the storage medium or device is read by the computer to perform the procedures described in this document. The system may also be considered to be implemented as a computer-readable storage medium, configured with a computer program, where the storage medium so configured causes a computer to operate in a specific and predefined manner.

Other embodiments are within the scope of the following claims. For example, a non-human entity such as a computer program may serve as a source for input information such as the connection table or as a recipient of output information such as diagrammatic data. In another example, one or more techniques based on the description herein may be applied to adapting structure diagrams for purposes other than presentation to a human user.

What is claimed is:

1. A computer-implemented method for use in deriving a chemical structure diagram, comprising:
    identifying, from a connection table for a chemical structure, an instance of chemical structural symmetry in the chemical structure;
    wherein the instance of chemical structural symmetry includes chemically symmetrically equivalent atoms and bonds;
    determining an arrangement of the chemically symmetrically equivalent atoms and bonds to provide a visually symmetric expression of the identified chemical structural symmetry in the chemical structure diagram;
    laying out the chemically symmetrically equivalent atoms and bonds in the chemical structure diagram in a two-dimensional pictorial representation of the chemical structure in accordance with the determined arrangement and outputting the pictorial representation of the chemical structure.
    outputting a representation of chemical structure.

2. The method of claim 1, wherein the identified instance of chemical structural symmetry is based on rotational symmetry.

3. The method of claim 1, wherein the identified instance of chemical structural symmetry is based on reflective symmetry.

4. The method of claim 1, wherein the identified instance of chemical structural symmetry is based on inversive symmetry.

5. The method of claim 1, further comprising:
    basing the identification of an instance of chemical structural symmetry on sterochemistry.

6. The method of claim 1, further comprising:
    basing the identification of an instance of chemical structural symmetry on rotational symmetry, reflective symmetry, and stereochemistry.

7. The method of claim 1, further comprising:
    basing the identification of an instance of chemical structural symmetry on double bond stereochemistry.

8. The method of claim 1, the determining an arrangement of the chemically symmetrically equivalent atoms and bonds further comprising:

determining a pivot point for the instance of chemical structural symmetry.

9. The method of claim 1, the determining an arrangement of the chemically symmetrically equivalent atoms and bonds further comprising:
determining a graph-theoretic center for the instance of chemical structural symmetry 10. The method of claim 1, the determining an arrangement of the chemically symmetrically equivalent atoms and bonds further comprising:
determining a symmetric order for the instance of chemical structural symmetry.

11. The method of claim 1, the determining an arrangement of the chemically symmetrically equivalent atoms and bonds further comprising:
determining whether an atom belongs to the identified instance of chemical structural symmetry.

12. The method of claim 1, the determining an arrangement of the chemically symmetrically equivalent atoms and bonds further comprising:
determining whether a bond belongs to the identified instance of chemical structural symmetry.

13. The method of claim 1, the determining an arrangement of the chemically symmetrically equivalent atoms and bonds further comprising:
in the event the identified instance of chemical structural symmetry is reflective, selecting a position for at least one of the chemically symmetrically equivalent atoms and bonds on an opposite side of a mirror line.

14. The method of claim 1, the determining an arrangement of the chemically symmetrically equivalent atoms and bonds further comprising:
in the event the identified instance of chemical structural symmetry is rotative, selecting a position for at least one of the chemically symmetrically equivalent atoms and bonds based on a pivot point.

15. The method of claim 1, the determining an arrangement of the chemically symmetrically equivalent atoms and bonds further comprising:
rotating the chemical structure diagram so that a mirror plane in the chemical structure diagram is horizontal.

16. The method of claim 1, the determining an arrangement of the chemically symmetrically equivalent atoms and bonds further comprising:
rotating the chemical structure diagram so that a mirror plane in the chemical structure diagram is vertical.

17. A computer-readable storage medium encoded with a set of instructions for use in a computer system to cause the computer system to derive a chemical structure diagram, the instructions causing the system to:
identify, from a connection table for a chemical structure, an instance of chemical structural symmetry in the chemical structure, wherein the instance of chemical structural symmetry includes symmetrically equivalent atoms and bonds;
determine an arrangement of the chemically symmetrically equivalent atoms and bonds to provide a visually symmetric expression of the identified chemical structural symmetry in the chemical structure diagram;
lay out the chemically symmetrically equivalent atoms and bonds in the chemical structure diagram in a two-dimensional pictorial representation of the chemical structure in accordance with the determined arrangement and output the pictorial representation of the chemical structure.

18. A computer-implemented method for use in deriving a chemical structure diagram, comprising:
identifying an instance of chemical structural symmetry in the chemical structure;
wherein the instance of chemical structural symmetry includes symmetrically equivalent atoms and bonds;
determining an arrangement of the chemically symmetrically equivalent atoms and bonds to provide a visually symmetric expression of the identified chemical symmetry in the chemical structure diagram;
laying out the chemically symmetrically equivalent atoms and bonds in the chemical structure diagram in a two-dimensional pictorial representation of the chemical structure in accordance with the determined arrangement and outputting the pictorial representation of the chemical structure.

19. The method of claim 18, wherein the identified instance of chemical structural symmetry is based on rotational symmetry.

20. The method of claim 18, wherein the identified instance of chemical structural symmetry is based on reflective symmetry.

21. The method of claim 18, wherein the identified instance of chemical structural symmetry is based on inversive symmetry.

22. The method of claim 18, further comprising: basing the identification of an instance of chemical structural symmetry on stereochemistry.

23. The method of claim 18, further comprising:
basing the identification of an instance of chemical structural symmetry on rotational symmetry, reflective symmetry, and stereochemistry.

24. The method of claim 18, further comprising:
basing the identification of an instance of chemical structural symmetry on double bond stereochemistry.

25. A computer-readable storage medium encoded with a set of instructions to cause a system to derive a chemical structure diagram, the instructions causing the system to:
identify an instance of chemical structural symmetry in the chemical structure, wherein the instance of chemical structural symmetry includes chemically symmetrically equivalent atoms and bonds;
determine an arrangement of the chemically symmetrically equivalent atoms and bonds to provide a visually symmetric expression of the identified chemical symmetry in the chemical structure diagram:
lay out the chemically symmetrically equivalent atoms and bonds in the chemical structure diagram in a two-dimensional pictorial representation of the chemical structure in accordance with the determined arrangement and output the pictorial representation of the chemical structure.

* * * * *